(12) United States Patent
Guimberteau et al.

(10) Patent No.: US 11,872,208 B2
(45) Date of Patent: Jan. 16, 2024

(54) COMPOSITION FOR TREATING PARASITES INFESTATIONS

(71) Applicant: CEVA SANTE ANIMALE, Libourne (FR)

(72) Inventors: Florence Guimberteau, Libourne (FR); Sandrine Lacoste, Libourne (FR); Romain Delcombel, Libourne (FR); Hamadi Karembe, Libourne (FR)

(73) Assignee: CEVA SANTE ANIMALE, Libourne (FR)

( * ) Notice: Subject to any disclaimer, the term of this patent is extended or adjusted under 35 U.S.C. 154(b) by 193 days.

(21) Appl. No.: 16/765,243

(22) PCT Filed: Nov. 23, 2018

(86) PCT No.: PCT/EP2018/082452
§ 371 (c)(1),
(2) Date: May 19, 2020

(87) PCT Pub. No.: WO2019/101971
PCT Pub. Date: May 31, 2019

(65) Prior Publication Data
US 2020/0306220 A1    Oct. 1, 2020

(30) Foreign Application Priority Data
Nov. 23, 2017 (EP) .................................... 17203186
Nov. 23, 2017 (EP) .................................... 17203187

(51) Int. Cl.
| | | |
|---|---|---|
| *A61K 31/366* | (2006.01) |
| *A61P 33/14* | (2006.01) |
| *A61K 9/00* | (2006.01) |
| *A61K 31/215* | (2006.01) |
| *A61K 47/02* | (2006.01) |

(52) U.S. Cl.
CPC .......... *A61K 31/366* (2013.01); *A61K 9/0014* (2013.01); *A61K 31/215* (2013.01); *A61K 47/02* (2013.01); *A61P 33/14* (2018.01)

(58) Field of Classification Search
CPC .................................................... A61K 31/366
See application file for complete search history.

(56) References Cited

U.S. PATENT DOCUMENTS

| | | | |
|---|---|---|---|
| 9,034,912 B1 * | 5/2015 | Taneja .................... | A01N 37/52 514/407 |
| 2007/0074640 A1 | 4/2007 | Romero Amaya et al. | |
| 2013/0231371 A1 * | 9/2013 | Nouvel ................ | A61K 31/415 514/404 |
| 2014/0221299 A1 * | 8/2014 | Leech ................ | A61K 31/7048 514/30 |
| 2016/0051524 A1 * | 2/2016 | de Rose ............ | A61K 31/4184 514/30 |
| 2016/0174556 A1 * | 6/2016 | Donnelly ............... | A01N 37/08 514/341 |

FOREIGN PATENT DOCUMENTS

| | | |
|---|---|---|
| WO | 2009/123907 A1 | 10/2009 |
| WO | 2013/152315 A1 | 10/2013 |
| WO | 2014/169092 A1 | 10/2014 |
| WO | 2016/183209 A1 | 11/2016 |

OTHER PUBLICATIONS

International Search Report and Written Opinion of corresponding application PCT/EP2018/082452, dated Feb. 11, 2019.

\* cited by examiner

*Primary Examiner* — Michael B. Pallay
(74) *Attorney, Agent, or Firm* — Leason Ellis LLP

(57) ABSTRACT

The present invention relates to a veterinary or pharmaceutical composition comprising: (i) about 1-65% w/v of a pyrethroid, or a salt thereof, (ii) a macrocyclic lactone, or a salt thereof, (iii) at least one alkalizing agent, (iv) at least one non aqueous solvent, wherein the pH of the composition is comprised between about 6.5 and 8.5, when measured by adding 25% of water to an aliquot of said composition. The invention further relates to the use of such composition for preventing and/or treating parasites infestations.

13 Claims, No Drawings

COMPOSITION FOR TREATING PARASITES INFESTATIONS

FIELD OF THE INVENTION

The invention relates to a veterinary or pharmaceutical composition comprising (i) about 1-65% w/v of a pyrethroid, or a salt thereof, (ii) a macrocyclic lactone, or a salt thereof, (iii) at least one alkalizing agent, (iv) at least one non aqueous solvent, wherein the pH of the composition is comprised between about 6.5 and 8.5, when measured by adding 25% v/v of water to an aliquot of said composition.

It is also related to a veterinary or pharmaceutical composition comprising (i) about 1-65% w/v of a pyrethroid, or a salt thereof, (ii) a macrocyclic lactone, or a salt thereof, (iii) at least one alkalizing agent, (iv) at least one non aqueous solvent, wherein the pH of the composition is comprised between about 6.5 and 8.5, when measured by adding 25% of water to an aliquot of said composition, for use in preventing and/or treating parasites infestations in a non-human mammal.

It also deals with a kit useful in preventing and/or treating parasites in a non-human mammal comprising a composition as described above, within a unique chamber pipette equipped with an applicator tip.

Finally, the invention deals with a method of treatment and/or prevention of parasites infestations in a non-human mammal, comprising administering to said non-human mammal a veterinary or pharmaceutical composition comprising (i) about 1-65% w/v of a pyrethroid, or a salt thereof, (ii) a macrocyclic lactone, or a salt thereof, (iii) at least one alkalizing agent, (iv) at least one non aqueous solvent, wherein the pH of the composition is comprised between about 6.5 and 8.5, when measured by adding 25% of water to an aliquot of said composition.

BACKGROUND OF THE INVENTION

Non-human mammals, for example companion animals such as dogs, puppies, cats, kitten, rabbits, mice, ferrets, horses, pigs . . . , are often subject to parasites infestations which feed on blood and therefore to infections caused by these parasites. These parasites may be ectoparasites, such as ticks, fleas, scabies, louses/nits, flies, mosquitoes . . . or endoparasites. Moreover, some of these parasites are intermediary hosts of endoparasites such as flatworms (or plathelminths), hookworms, whipworms or roundworms (or nematodes).

More particularly, heartworm is a parasitic roundworm (especially *Dirofilaria immitis*) that spreads from host to host through bites of mosquitoes (intermediate host). The definitive and most affected hosts are dogs but it can also infect cats, wolves, coyotes, foxes, ferrets, sea lions and even bovines and humans. It is found in the five continents.

The parasite is commonly called "heartworm" because the adult reproductive stage of its life cycle resides primarily in the right ventricle of its host where it can live for many years. Heartworms infection may result in serious diseases for the host: dirofilariasis, and more precisely, heartworm disease.

When a mosquito bites an infected animal, young heartworms, called microfilariae, enter the mosquito's blood system. Within two weeks, the microfilariae develop into infective larvae inside the mosquito and these infective larvae can be transmitted to other animals when mosquito bites again.

When entering the dog's blood system via this bite, larvae develop (macrofilariae) and migrate to the dog's heart where they mature and breed. The dirofilaria life cycle is completed when the ingested microfilariae mature into infective larvae in the mosquito. Development of larvae into adult worms takes about 180 days in dogs, while, the life cycle of heartworms is approximately 6 months.

*Dirofilaria immitis* appears as white threadlike round worms reaching up to 20 cm long for adult males (12-20 cm) and 31 cm for adult females (25-31 cm), with a mean diameter of 1 mm.

Heartworms are primarily found in the pulmonary artery in dogs with low parasitic burden (<50 worms). In infestations with high parasitic burden (>50 worms), worms may reach the right ventricle, right atrium, and occasionally vena cava. The initial response includes swelling of small pulmonary arteries and blood clotting. The physical presence of heartworms in the pulmonary artery and right ventricle of the canine heart, and the resulting destruction of tissue, causes respiratory and circulatory problems which can be fatal under conditions of stress or vigorous exercise. Pulmonary hypertension and right-sided heart failure may result in congestive heart failure.

Because a lot of heartworms are necessary to clog up blood flow to a significant degree, heartworms can be present inside the heart for up to 2 or 3 years before causing clinical signs. As the disease progresses, lung tissue can be destroyed leading to a worsening cough while liver and kidney damages can occur due to reduced blood flow in organs. If left untreated, heartworm disease may result in death.

Even though safe, highly effective and convenient prevention strategies have been available for the past two decades, heartworm disease, due to *Dirofilaria immitis*, continues to cause severe damages and even death in dogs and other mammals (cats, bovines, humans, guinea porcine, and ferrets) in many parts of the world. Moreover, the parasite and vector mosquitoes continue to spread into areas where they have not been reported previously.

Another roundworm which can be cited is *Dirofilaria repens*. It is most often found in Eastern Europe, Africa and Asia. The worm affects dogs and other carnivores such as cats, wolves, sea lions, foxes, coyotes and muskrats. As with *Dirofilaria immitis* worm, mosquitoes (host and vector) transmit infectious microfilariae, which develop into fertile macrofilariae in their definitive host: the dog. Larvae develop into infective larvae within the mosquito over 10-16 days, before being reintroduced back into a new host. The adults of *Dirofilaria repens* are located in the subcutaneous tissues of dogs and cats, where they mature in 6-7 months. *Dirofilaria repens* appears as white threadlike round worms reaching up to 25 cm long for adult females (25-30 cm) whereas adult males are shorter, with a mean diameter of 1-2 mm.

In both cases (*Dirofilaria repens* and *Dirofilaria immitis*), humans may also become infected as aberrant hosts. But, most infective larvae introduced in human die.

Currently, only two arsenic derivatives are available for curative treatment of clinically infested dogs. First, thiacetarsamide (Caparsolate®, by Abbott Laboratories) which is an old medication, with severe adverse effects and second, melarsomine dihydrochloride (Immiticide®, by Merial or Diroban®, by Zoetis), which is a more recent drug with fewer side effects. For chemoprophylaxis, two alternatives are possible to prevent heartworm disease in dogs: daily administration of diethylcarbamazine citrate, or monthly administration of macrocyclic lactones.

Alike, fleas and ticks can cause serious discomfort or diseases (babesiosis, leishmaniosis, bartonellosis, anaplasmosis, ... ). For example, *Ctenocephalides* fleas (or lice) are intermediary hosts of *Dipylidium caninum* (also called flea tapeworm, double-pore tapeworm, or cucumber tapeworm) which is an intestinal parasite in dogs and cats. This infestation can cause an anal pruritus, anal bags congestion, or a perineal region dermatitis.

As such, ticks (*Ixodes, Haemophilus, Dermacentor, Rhipicephalus, Amblyomma*, ... ) can cause stress or be harmful to the animal. One of the major problems is the transmission of pathogen agents. Serious diseases can occur: borelliosis (Lyme disease, *Borellia burgdorferi*), babesiosis (piroplasmosis, *Babesia* sp.), leishmaniosis, rickettsiosis ... Ticks can also deliver crippling, inflammatory and sometimes deadly toxins.

Finally, scabies (*Demodex* sp., *Sarcoptes* sp., *Otodectes* sp., ... ) are hard to control/kill because only few efficient treatments do exist, and the infected animal has to be frequently treated.

The control of such parasites has long been recognized as an important aspect of human and animal health regimens. Although a number of alternatives to control infestations are in use, they suffer from many problems, including a limited spectrum of activity, the need of repeated treatment (lack of compliance) and, in some rare instances, resistance by parasites, in particular with the use of carbamates, organophosphorous compounds or pyrethroids. That is why it is very important to develop new efficient treatments.

Number of macrocyclic lactones have been commercialized as treatment to such parasites, for example ivermectin under the name of Ivomec® or Heartgard® (by Merial), doramectin (Dectomax®, by Zoetis), selamectin (Stronghold®, by Zoetis), moxidectin and abamectin (Avomec®, by Merial).... As another example, a slow release formulation of subcutaneously injected moxidectin-impregnated lipid microspheres, providing continuous protection against dirofilaria of six months following a single dose administration, has been marketed by Zoetis under the name of Moxidectin SR®, ProHeart 6® or Guardian SR®. It is a suspension which requires a complex preparation and use in general veterinary practice and which does not protect against fleas, ticks and mosquitoes. Besides, this product has been voluntarily removed from the US market in September 2004 because of safety related issues, and currently has been allowed once again by FDA under a risk minimization and restricted distribution program.

Afoxolaner is commercialized by Merial (Nexgard®) against fleas and ticks, in dogs, but is not repellent: parasites must bite the dog to be exposed to the active substance. Consequently, the transmission risk of parasites diseases (for example heartworm disease caused by dirofilaria) cannot be excluded.

A composition of imidacloprid and moxidectin is commercialized by Bayer (Advocate®) to treat cats against fleas, ticks and prevent dirofilariasis but is not repellent.

A composition of imidacloprid and permethrin is commercialized by Bayer (Advantix®) to treat dogs against fleas, ticks and mosquitoes but is not efficient against internal parasites such as dirofilaria. Selamectin spot-on is commercialized by Zoetis (Revolution®) to kill adult fleas and prevents flea eggs from hatching for one month and is indicated for the prevention and control of flea infestations (*Ctenocephalides felis*), prevention of heartworm disease caused by *Dirofilaria immitis*, and to treat and control ear mite (*Otodectes cynotis*) infestations. Revolution® is also indicated for the treatment and control of roundworm (*Toxocara cati*) and intestinal hookworm (*Ancylostoma tubaeforme*) infections in cats. The recommended minimum dose is 2.7 mg selamectin per pound (6 mg/kg) of body weight. Once again, this product is not repellent, especially to mosquitoes or sandflies, which have to bite the animal to be exposed to selamectin.

US2013231371 relates to a spot-on pesticidal composition comprising between about 0.25% to about 60% (w/w) pyrethroid and about 0.01% to about 10% (w/w) macrocyclic lactone, but the document does not disclose the specific combination moxidectin/permethrin. Moreover, the composition as such is not stable (see example 1, Z32, of the present application).

WO2013119442 describes a soft chewable composition comprising an isoxazoline, permethrin and optionally moxidectin (0.5% w/w maximum). It is difficult to foresee the composition performances because they depend on the absorption by the mammal, and it comprises an isoxazoline and only optionally moxidectin: in this case, this composition is not endectocide.

Main weaknesses of the existing products and the latest developments are the lack of repellency activity, the lack of protection against ticks (for example Advocate®), and the lack of synergetic association of two molecules to generate a chemically stable composition which is simultaneously endectocide and repellent and protects against heartworm in one single application, and which is long acting.

Indeed, none of the prior art documents disclose a stable composition comprising a macrocyclic lactone and a pyrethroid, in a chemically stable composition, which is useful to simultaneously treat and/or prevent endo- and ectoparasites infestations in non-human mammals, and which is in addition repellent.

SUMMARY OF THE INVENTION

Consequently, in order to overcome the foregoing problems, namely, to produce a composition with an increased killing efficiency against endoparasites and ectoparasites, to eradicate dirofilariasis, to repel ectoparasites, to provide more predictable performances, to produce an easy-to-use and long acting composition, to produce a stable composition comprising a pyrethroid and a macrocyclic lactone, and finally to produce this kind of composition which is moreover chemically stable and which does not degrade over time, there is a need in the art for a new composition which affords improved absorption and bioavailability, at a lower maximum plasma concentration.

Therefore, the present invention aims to provide a novel formulation which combines ectoparasites repellency and killing: ticks, fleas, mosquitoes, sandflies, mites, mange, lice, and killing of endoparasites (roundworms, hookworms, heartworms, tapeworms and whipworms), and which is very easy to administer (spot-on or line-on) and is able to maintain an effective plasma concentration over a long period.

The composition according to the present invention has numerous advantages compared to prior art. It is safer, not toxic, well accepted and chemically stable. There are neither relevant local (no red blotches, no hair loss, no itching, no scaling, limited cosmetic effect ... ) nor general negative clinical signs (biochemistry/biology) due to the use of the composition, but an acceptable local and general tolerance by the mammal.

Due to the combination action of the pyrethroid/macrocyclic lactone according to the present invention, the composition is more effective. Hence, only a single application is useful, once every months. The composition has a good dermal permeation of moxidectin (higher than market products).

The composition according to the present invention is also ready-to-use. It is easy to use as a veterinary medicine: the user neither needs to prepare any suspension or solution, nor need to measure/calculate and extract the convenient amount of drug from a syringe, according to the weight of the animal, hence, the composition can be easily topically applied by the animal owner, in a single application, and no more necessary by a veterinarian. It is a ready-to-use spot-on/line-on composition. Consequently, there is no risk of dose error. The dosage regimen is perfectly controlled thanks to the ready-to-use pipette, resulting in a better observance of the treatment.

One more advantage is that the composition according to the present invention is safe in multi-drug resistance (MDR-1) gene deficient dogs, compared to most compositions comprising macrocyclic lactones, and can therefore be administered to these dogs.

Moreover, the composition according to the present invention has a good pharmacokinetic profile in mammals, especially, in dogs and cats and has a tremendous effectiveness against gastrointestinal and respiratory nematodes.

The particular advantage of the composition according to the present invention is its double protection against mosquitoes and heartworms. It is the only endectocide which is repellent and in the same time, the only topical endectocide which kill and repels ticks. There is a complete protection against heartworm and mosquitoes with only one single application.

Moreover, the topical (spot-on, line-on) administration increases the composition efficiency: there is a better protection than with a monthly oral administration (Blagburn, 2011). More particularly, the "line-on" application allows the control of the active ingredients diffusion: the composition is administered externally against the grain of the animal and applied continuously.

Therefore, the problem solved by the present invention, is to provide a chemically stable veterinary or pharmaceutical composition which comprises a pyrethroid in association with a macrocyclic lactone which is easily applied to treat and/or prevent parasites infestations in a non-human mammal, which is repellent and endectocide, which is efficient and allows an efficient plasma concentration during one month, or more.

In a first aspect, the object of the present invention is a veterinary or pharmaceutical composition comprising (i) about 1-65% w/v of a pyrethroid, or a salt thereof, (ii) a macrocyclic lactone, or a salt thereof, (iii) at least one alkalizing agent, (iv) at least one non aqueous solvent, wherein the pH of the composition is comprised between about 6.5 and 8.5, when measured by adding 25% of water to an aliquot of said composition.

In a preferred aspect, the object of the present invention is a veterinary or pharmaceutical composition comprising (i) about 25-65% w/v of permethrin, or a salt thereof, (ii) a macrocyclic lactone, or a salt thereof, (iii) at least one alkalizing agent, (iv) at least one non aqueous solvent, wherein the pH of the composition is comprised between about 6.5 and 8.5, when measured by adding 25% of water to an aliquot of said composition.

A further object of the invention is a veterinary or pharmaceutical composition (i) about 1-65% w/v of a pyrethroid, or a salt thereof, preferably about 25-65% w/v of permethrin, or a salt thereof, (ii) a macrocyclic lactone, or a salt thereof, (iii) at least one alkalizing agent, (iv) at least one non aqueous solvent, wherein the pH of the composition is comprised between about 6.5 and 8.5, when measured by adding 25% of water to an aliquot of said composition, for use in preventing and/or treating parasites infestations in a non-human mammal.

A third object of the invention is to provide a kit useful in preventing and/or treating parasites in a non-human mammal comprising a composition as described above, within a unique chamber pipette equipped with an applicator tip.

Finally, the invention discloses a method of treatment and/or prevention of parasites infestations in a non-human mammal, comprising administering to said non-human mammal a veterinary or pharmaceutical composition comprising (i) about 1-65% w/v of a pyrethroid, or a salt thereof, preferably about 25-65% w/v of permethrin, or a salt thereof, and (ii) a macrocyclic lactone, or a salt thereof, (iii) at least one alkalizing agent, (iv) at least one non aqueous solvent, wherein the pH of the composition is comprised between about 6.5 and 8.5, when measured by adding 25% of water to an aliquot of said composition.

DETAILED DESCRIPTION OF THE INVENTION

In a first aspect, this invention relates, to a veterinary or pharmaceutical composition comprising: (i) about 1-65% w/v of a pyrethroid, or a salt thereof, preferably about 25-65% w/v of permethrin, or a salt thereof, and
  (ii) a macrocyclic lactone, or a salt thereof,
  (iii) at least one alkalizing agent,
  (iv) at least one non aqueous solvent,
wherein the pH of the composition is comprised between about 6.5 and 8.5, when measured by adding 25% of water to an aliquot of said composition.

Within the context of invention, "at least" means one or more, for example "at least one alkalizing agent" means one alkalizing agent or more than one alkalizing agent, for example two or three alkalizing agents.

Weight by volume as used herein or % w/v means % weight by volume of the total composition, more precisely w/v is the mass concentration defined as the mass of a constituent divided by the volume of the mixture. For example, 65% w/v is equal to 650 mg/mL. In a preferred embodiment, the amount of pyrethroid is 20 times superior to the macrocyclic lactone amount.

Volume by volume as used herein or % v/v means % volume by volume of the total composition, more precisely v/v is the volume fraction which is defined as the volume of a constituent V divided by the volume of all constituents of the mixture prior to mixing.

Within the context of invention "pharmaceutical composition" refers to a composition containing drugs used to treat and/or diagnose and/or cure and/or prevent diseases. Furthermore, a drug is any substance or combination of substances (composition) presented as having properties to treat and/or prevent disease(s) in human beings; or any substance or combination of substances which may be used in, or administered to human beings either with a view to restoring, correcting or modifying physiological functions by exerting a pharmacological, immunological or metabolic action, or to making a medical diagnosis (according to the Directive 2004/27/EC).

According to the FDA glossary, within the context of invention "pharmaceutical composition" also refers to a "drug product" which is the finished dosage form that contains a drug substance, generally, but not necessarily in association with other active or inactive ingredients.

A drug is defined as a substance recognized by an official pharmacopoeia or formulary, a substance intended for use in the diagnosis, cure, mitigation, treatment, or prevention of disease, a substance (other than food) intended to affect the structure or any function of the body, a substance intended for use as a component of a medicine but not a device or a component, part or accessory of a device (biological products are included within this definition and are generally covered by the same laws and regulations, but differences exist regarding their manufacturing processes-chemical process versus biological process-).

According to the present invention the term "veterinary" has the same definition as "pharmaceutical", but adapted to animals (meaning non-human beings): "animal" means any living stage of any member of the animal kingdom except human beings. More precisely, a "veterinary drug" (or medicine or composition) means any substance or mixture of substances which is used, or is manufactured, sold or represented as suitable for use, in the diagnosis, treatment, control, eradication, mitigation or prevention of disease or abnormal physical or mental state or the symptoms thereof in an animal; or restoring, correcting, controlling, or modifying any physical, mental or organic function in an animal.

The composition as disclosed herein is a stable composition. As used herein, "stable composition" refers to the chemical stability which means a thermodynamic stability of the chemical composition: the composition is in its lowest energy state, or chemical equilibrium with its environment. This may be a dynamic equilibrium, where individual atoms or molecules change form, but their overall number in a particular form is conserved. This type of chemical thermodynamic equilibrium will persist indefinitely unless the composition is changed. The composition is "chemically balanced": the chemical equilibrium is the state in which both reactants and products are present in concentrations which have no further tendency to change with time. Usually, this state results when the forward reaction proceeds at the same rate as the reverse reaction. The reaction rates of the forward and backward reactions are generally not zero, but equal. Thus, there are no significant changes in the concentrations of the reactants and products. The composition does not degrade over time and is equally efficient after many weeks or months of storage.

Macrocyclic lactones are classified in two groups of structurally related molecules: milbemycins and avermectins (ivermectin, doramectin, abamectin, eprinomectin and selamectin). The first veterinary macrocyclic lactone, ivermectin, was introduced as an antiparasitic drug in 1981 and its tremendous efficacy against nematodes and arthropods took parasite control to a new level. Heartworms (L3 and L4 larvae) are particularly sensitive to macrocyclic lactones.

However, it was early discovered that certain breeds of dog with MDR-1 deficiency are highly susceptible to the toxic effects of macrocyclic lactones. A well-known sensitive breed is the collie dog. Therefore, the maximal tolerated dose in collie and related dogs dictates the acceptable therapeutic dose range.

More particularly, ivermectin has a narrow safety margin on sensitive dogs. Therefore, its use is restricted to the prevention of heartworm (6 µg/kg per os or 80 µg/kg topically). Ivermectin does not possess clinically relevant activity against ticks and fleas infesting dogs. Selamectin is well tolerated in MDR1-deficient dogs. It is the only macrocyclic lactone with curative and preventive activities against fleas (adulticide and insect growth regulator like effects). Selamectin has also an acaricidal activity, which is clinically limited by the slow onset of action (3 to 5 days), the narrow spectrum (*Dermacentor variabilis* and *Rhipicephalus sanguineus*) and the need of frequent applications: weekly or every two weeks. Milbemycin oxime is applied only per os (tablets) and is well tolerated by MDR1-deficient dogs. It is a pure nematocidal drug, active against adult stages of gastrointestinal nematodes. However, *Uncinaria stenocephala* is refractory to milbemycin oxime when given at the recommended dose rate. Milbemycin oxime is also of value in the control of French heartworm (*Angiostrongylus vasorum*), when applied four times at weekly intervals. Moxidectin is applied orally for the prevention of heartworm (3 µg/kg) and topically for the control of and gastrointestinal and respiratory nematodes. Topical application is safe in collie dogs. Moxidectin has a tremendous efficacy against gastrointestinal and respiratory nematodes (adults, immature adults and L4 stages). The recommended monthly application is also effective against respiratory nematodes. Moxidectin is the ideal macrocyclic lactone for the control of gastrointestinal and respiratory nematodes of dogs.

Milbemycins are used as antiparasitic agents against worms, ticks and fleas. According to the present application, milbemycins (or milbemycin) mean milbemycin oxime, moxidectin, or mixtures thereof, and more preferably the macrocyclic lactone is moxidectin.

Moxidectin (or milbemycin B) has the structural formula (milbemycin B, cas no 11350706-5, molecular weight 639.8 g·mol$^{-1}$):

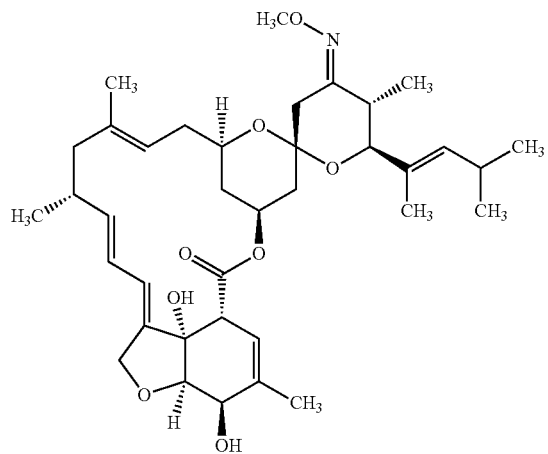 [SMILES: CO/N=C1\C[C@]2(C[C@@H]3C[C@@H](C/C=C(\C)C[C@@H](C)/C=C/C=C4\CO[C@@H]5[C@H](O)C(C)=C[C@@H](C(=O)O3)[C@]45O)O2)O[C@H](/C(C)=C/C(C)C)[C@H]1C]

More particularly, the amount of macrocyclic lactone, or a salt thereof, is comprised in an amount of about 0.05 and 25% weight by volume (w/v) of the composition, especially between 1-10% w/v, especially between 2-5% w/v, especially between 2-2.5% w/v, more preferably the macrocyclic lactone is present in an amount of 2.5% w/v of the total composition, and the preferred macrocyclic lactone is moxidectin.

Composition according to the present application further comprises a pyrethroid. "Pyrethroid(s)" includes organic compound similar to the natural pyrethrins produced by the pyrethrums flowers (*Chrysanthemum cinerariaefolium* and *Chrysanthemum coccineum*). Pyrethroids are insecticide, have repellent properties and are generally harmless to humans. Different types of pyrethroids can be chosen for the composition of the present application: allethrin, bifenthrin, cyfluthrin, cypermethrin, cyphenothrin, deltamethrin, esfenvalerate, etofenprox, fenpropatrhin, fenvalerate, flucythrinate, flumethrin, heptafluthrin, imiprohrin, lambda cyaholtrhin, meperfluthrin, metofluthrin, momfluorothrin, permethrin, prallethrin, profluthrin, resmethrin, silfluofen, sumithrin, tau-fluvalinate, tefluthrin, tetramethrin, tetramethylfluthrin, tralomethrinand transfluthrin. More specifically, the pyrethroid according to the present application are deltamethrin or metofluthrin or momfluorothrin or flumethrin or permethrin. Even more specifically, the pyrethroid according to the present application is permethrin.

The structural formula of permethrin (Nix®, cas no 52645-53-1, molecular weight 391.29 g·mol$^{-1}$) is:

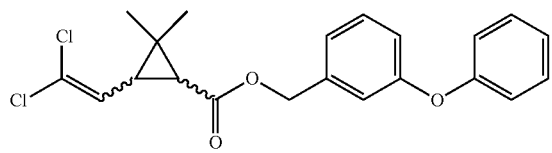 [SMILES: CC1(C)C(C=C(Cl)Cl)C1C(=O)OCc1cccc(Oc2ccccc2)c1]

Permethrin (or (±)-3-phenoxybenzyl 3-(2,2-dichlorovinyl)-2,2-dimethylcyclopropanecarboxylate) has four stereoisomers (two enantiomeric pairs), thanks the two stereocenters in the cyclopropane ring (see below). The trans enantiomeric pair is known as transpermethrin.

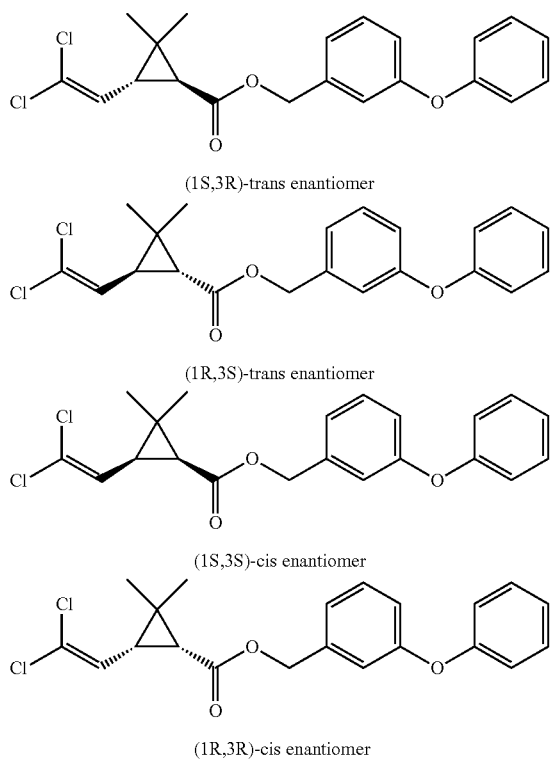

(1S,3R)-trans enantiomer (1R,3S)-trans enantiomer (1S,3S)-cis enantiomer (1R,3R)-cis enantiomer According to the present invention, permethrin is an isomeric mixture comprising a cis/trans ratio of about 40/60, which means a cis/trans ratio of 36-44/66-56, or of 40/60. The term "cis" refers herein to a mixture of (1S, 3S) and (1R, 3R) isomers and the term "trans" refers herein to a mixture of (1R, 3S) and (1S, 3R) isomers.

In the present application, the term "about" includes all values within a range of 10% of the stated number (above or below the numerical value), especially all values within a range of 8% of the stated number, more especially all values within a range of 6% of the stated number, more especially all values within a range of 5% of the stated number, more especially all values within a range of 4% of the stated number, more especially all values within a range of 3% of the stated number, more especially all values within a range of 2% of the stated number, and even more especially all values within a range of 1% of the stated number.

More particularly, the amount of pyrethroid, or a salt thereof, is comprised between 1 and 65% w/v of the composition, especially between 5-60% w/v, especially between 10-55% w/v, especially between 15-55% w/v, especially between 20-55% w/v, especially between 25-52% w/v, especially between 35-51% w/v, especially between 35-50% w/v, especially between 45-50% w/v, or equal to 50% w/v of the composition. In a preferred embodiment, the pyrethroid is permethrin. In a more preferred embodiment, the amount of permethrin, or a salt thereof, is comprised between 25 and 65% w/v of the composition, especially between 30-60% w/v, especially between 30-55% w/v, especially between 40-55% w/v, especially between 45-55% w/v, especially between 45-52% w/v, especially between 45-51% w/v, especially between 45-50% w/v, especially between 48-50% w/v. More preferably, the permethrin is present in an amount of at least 45% w/v of the total composition, or equal to 50% w/v of the total composition.

The terms macrocyclic lactones (including milbemycin) and pyrethroids (including permethrin) also comprise their pharmaceutically acceptable salts. The salt can be hydrochloride, hydrobromide, phosphate, nitrate sulfate, fumarate, citrate, tartrate, acetate, maleate, toluenesulfonate, methanesulfonate, or mixtures thereof and the like.

Moreover, the inventors surprisingly found that the addition of an alkalizing agent to the composition of the present invention, and the stabilization of the pH between 6.5 and 8.5 stabilizes the aforesaid composition. The concentrations of pyrethroid, alkalizing agent and macrocyclic lactone, and the acidity control according to the present invention allow to efficiently stabilize the resulting composition.

Therefore, the composition according to the present invention comprises at least one alkalizing agent. Within the context of the invention, "alkalizing agent" refers to a base (weak, strong) used to maintain the pH (potential of hydrogen: acidity or basicity) of a solution near a particular value after the addition of another base. The function of a buffer agent is to chemically balance a solution by preventing a rapid change in pH when acids or bases are added. According to the present invention, alkalizing agents include sorbate buffers (potassium sorbate, sodium sorbate . . . ), phosphate buffers (potassium phosphate monobasic, sodium phosphate dibasic . . . ), carbonate buffers (calcium carbonate, sodium carbonate, ammonium carbonate . . . ), bicarbonate buffers (sodium bicarbonate . . . ), sodium borate, potassium hydroxide, potassium citrate, sodium lactate, calcium acetate, diethanolamine, monoethanolamine, trolamine, ammonia solution, sodium hydroxide, or mixtures thereof. One or more alkalizing agents can be present in the composition. According to the present invention, the preferred alkalizing agent is sodium hydroxide, potassium sorbate or potassium hydroxide, and even more especially sodium hydroxide.

As the drug composition according to the present invention is non-aqueous, a direct conventional pH measurement is not possible. Therefore, the pH of the composition according to the present invention is adjusted so as to be comprised between about 6.5 and 8.5, when measured by adding 25% of water to an aliquot of said composition. For the measure of the pH of the composition, which means the final composition comprising active components and excipients, the following method is used: in a centrifuge tube, 75 v % (% volume) of drug composition and 25 v % of purified water are added. The blend is homogenized using a vortex equipment, then centrifuged and the pH of the upper phase (which means the water based phase) is determined. The pH of the final drug composition must be comprised between 6.5 and 8.5, preferably 6.8 and 8.0, more preferably 7.0 and 8.0, 7.1-8.0, 7.2-8.0, 7.2-7.9, 7.2-7.8.

Before determining the final drug composition pH, the pyrethroid (permethrin) pH must be checked: in a centrifuge tube 37.5 v % of drug substance, 37.5 v % of benzyl alcohol and 25 v % of purified water are added. The blend is homogenized using a vortex equipment, then centrifuged and the pH of the upper phase (which means the water based phase) is determined.

In addition of the pH measurement, the acid value can be determined. The acid value (IA) is the number that expresses, in milligrams the quantity of potassium or sodium hydroxide required to neutralize the free acids present in 1 g of the substance. To determine the acid value, the following method, according to the European pharmacopeia chapter 2.5.1 is used:

Dissolve 10.00 g of the substance to be examined, or the quantity prescribed (m in g), in 50 mL of a mixture of equal volumes of ethanol (96 percent) R and light petroleum R3, previously neutralized with 0.1 M potassium hydroxide or 0.1 M sodium hydroxide, unless otherwise specified, using 0.5 mL of phenolphthalein solution R1 as indicator. If necessary, heat to about 90° C. to dissolve the substance to be examined. When the substance to be examined has dissolved, titrate with 0.1 M potassium hydroxide or 0.1 M sodium hydroxide until the pink colour persists for at least 15 seconds (n mL of titrant). When heating has been applied to aid dissolution, maintain the temperature at about 90° C. during the titration. The IA is calculated with the formula: IA=5.611×n/m.

In the context of the present invention, the determination of the IA helps to adjust the amount of alkalizing agent to reach the targeted pH.

Another object of the invention is a method of manufacturing the composition as described above, comprising the steps of:
(i) determining acid value (IA) of the pyrethroid,
(ii) mixing all the components,
(ii) adding in the composition about 0.0001×IA to 0.01× IA mg/mL of at least one alkalizing agent for each mg/mL of pyrethroid.

The amount of alkalizing agent depends on the permethrin final grade, permethrin purity grade and permethrin acidity. The preferred alkalizing agent is sodium hydroxide, and more especially a sodium hydroxide solution at 32 wt % (32 g of soda for 100 g of solution). The alkalizing agent is present in an amount comprised between about 0.0001% w/v to 1% w/v of the total composition, preferably between about 0.001% w/v to 0.5% w/v, between about 0.001% w/v to 0.3% w/v, between about 0.001% w/v to 0.16% w/v, even more preferably about 0.001, 0.01, 0.025, 0.12, or 0.16% w/v.

Furthermore, the composition according to the present invention include one or more of the following non aqueous solvents (polar, apolar, protic, aprotic) which is/are selected from: benzyl alcohol, dimethylsulfoxyde (DMSO), N-octyl-2-pyrrolidone (NOP), N-methyl-2-pyrrolidone (NMP), propylene carbonate, transcutol (2-(2-ethoxyethoxy)ethanol or highly purified diethylene glycol monoethyl ether), acetone, 2-butanone, 3-methyl-2-butanone, cyclohexanone, acetonitrile, xylene, chlorobenzene, methylene chloride, chloroform trichloroethane, benzaldehyde ethylene chloride, sulfolane, methyl tert-butyl ether, dibutyl ether, ethyl acetate, acetate propyl methacrylate, amyl acetate, propyl acetate, dimethylformamide (DMF), dimethylacetamide (DMAC), propylene diethylcarbonate, ethylene carbonate, acetonitrile, triethylamine, pyridine, methanol, ethanol, isopropanol, hexafluoroisopropanol, carboxylic acids such as formic acid and acetic acid, primary and secondary amines, propylene alkyl ether, ethylene alkyl ether, polyglycol alkyl ether, di polyglycol allyl, polypropylene glycol, polyethylene glycol . . . and mixtures thereof. The preferred solvents are benzylalcohol, DMSO, NOP, NMP, propylene carbonate, and/or transcutol (2-(2-ethoxyethoxy)ethanol or highly purified diethylene glycol monoethyl ether). In a particular embodiment, the composition comprises a solvent such as benzyl alcohol, transcutol or NMP. In another preferred embodiment, the composition comprises the non aqueous solvents: benzyl alcohol and/or purified diethylene glycol monoethyl ether and/or NMP.

The solvent or the mixture of solvents are present in an amount of between 0.5% w/v and 98.95% w/v of the total composition. Propylene carbonate is present in a preferred amount of about 8.3% w/v of the total composition. In another embodiment, DMSO is present in a preferred amount of 3% w/v of the total composition. In another embodiment NOP is present in a preferred amount of 6.6% w/v of the total composition, and quantum satis (QS) of benzyl alcohol.

Furthermore, the composition according to the present invention may further include any of the following other excipients in a pharmaceutically acceptable amount such as, for example, one or more: antioxidants, flowing agents, dyes, lubricants, diluents, preservatives, crystallization inhibitors, colloids, adhesives, thickeners, thixotropic agents, penetrating agents, stabilizers, solubilizing agents, fluidizing agents, complexing agents, vitamins, minerals, antiseptic agents, or combinations thereof. More generally, the active ingredients may be combined with any solid or liquid additives corresponding to the usual technologies of formulation development.

An excipient, or auxiliary substance, refers to any drug component which is not an active substance (such as adjuvants, stabilizers, diluents, antioxidants, antimicrobial preservatives . . . ), according to pharmacopeias.

Antioxidant(s), when present in the composition, may be selected from: 2,6-di-tert-butyl-4-methylphenol (butyl hydroxytoluene or BHT), vitamin E (DL-alpha-tocopherol, E307), vitamin E phosphate, vitamin A, ascorbic acid (vitamin C), vitamin B12, polyphenols, butyl hydroxyanisol (BHA), propylgallate, tocopherol, ascorbic acid, citric acid, di-alpha-tocopheryl phosphate, beta-carotene, carotenes, carotenoids, flavonoids, sulfate compounds, L-cysteine, thiodipropionic acid, thiolactic acid, monothioglycerol, propyl galate sodium metabisulfite, sodium formaldehyde, sulfoxylate acetate, and mixtures thereof. The preferred antioxidant is BHT. Antioxidants/antioxidant are/is present in an amount of between 0.001 and 2%, more preferably is present in an amount of 0.05% w/v of the composition, or the amount of antioxidant can be 0% (no antioxidant).

Preservatives may be selected from: methyl p-hydroxybenzoate, ethyl p-hydroxybenzoate, phenol, sorbic acid, cresol and chlorocresol, and mixtures thereof. Preservatives are present in an amount of 0.001-5% w/v of the composition, or the amount of preservatives can be 0% (no preservative).

Illustrative thickening agents include methylcellulose, hydroxyethyl methyl cellulose, hydroxy methyl cellulose, ethyl cellulose, hydroxyethyl cellulose, sodium carboxymethyl cellulose, hydroxypropyl cellulose, polyvinylpyrrolidone, calcium carboxymethylcellulose, hypromellose, povidone, polyethylene glycol, carbomers, polyvinyl alcohol, polyethylene oxide, polymethacrylates, and mixtures thereof. Thickening agents are present in an amount of about 0-10% w/v of the composition, more preferably 0-8% w/v, more preferably 0-6% w/v, even more preferably 0-5% w/v of the composition.

Illustrative complexing agents include EDTA and salts thereof, phosphate, nitrate, acetate, citrate, and mixtures thereof.

Illustrative antiseptics include methyl p-oxybenzoate, propyl p-oxybenzoate, PHB ester, chlorobutanol, benzyl alcohol, butanol, butane-1,3-diol, chlorohexidin salts, benzoic acid and its salts, sorbic acid, and mixtures thereof.

Furthermore, the composition according to the present invention further comprises one or more additional active substances like ectoparasitic or endoparasitic control agents, antibiotics, non steroidal anti-inflammatory drugs, etc.

An active substance refers to any substance intended to be used to prepare a medicine, and, when it is used in the manufacture of the medicine, becomes an active substance of this medicine, such substances are intended to supply a pharmacological activity or another direct effect for the disease, diagnosis, healing, attenuation, treatment or prevention or to produce an effect on the body structure and function (as defined in pharmacopeias).

Preferred ectoparasitic agents according to the present invention are selected from: organochlorines, organophosphates, formamidines, amidines, carbamates, pyrethroids (cypermethrin, flumethrin . . . ) pyrethrins, phenylpyrazoles (fipronil, pyriprole . . . ), benzoylureas, neonicotinoids (dinotefuran, imidacloprid, nitenpyram . . . ), oxadiazines, spinosyns (spinosad, spinetoram), isoxazolines (afoxolaner, fluralaner, lotilaner, sarolaner), cholinesterase inhibitors, insect growth regulators (fluazuron, methoprene, pyriproxifen, triflumuron, lufenuron, novaluron, chlorfluazuron, hydroprene), and the like, or mixtures thereof. The preferred ectoparasitic agent is fipronil.

Preferred endoparasitic agents according to the present invention are selected from: benzimidazoles (enbendazole, oxfendazole, albendazole, triclabendazole), imidazothiazoles (levamisole, tetramisole), pyrimidines (pyrantel, pyrantel tartrate), isoquinolines (praziquantel, epsiprantel), salicylanilides (closantel, niclosamide, oxyclozanide, rafoxanide), tetrahydropyrimidines, amino-acetonitrile derivatives, depsipeptides, spiroindoles, and the like, or mixtures thereof. The preferred endoparasitic agent is oxyclozanide, or selamectin, or mylbemycin, or praziquantel.

In the most preferred embodiment the present invention refers to a veterinary or pharmaceutical composition comprising:
 (i) about 1-65% w/v of a pyrethroid, or a salt thereof, wherein the pyrethroid is preferably an isomeric mixture comprising a cis/trans ratio of about 40/60,
 (ii) a macrocyclic lactone, or a salt thereof, wherein the macrocyclic lactone is present in an amount of about 0.05-25% w/v of the total composition, and is preferably moxidectin
 (iii) at least one alkalizing agent, wherein the alkalizing agent is preferably sodium hydroxide,
 (iv) at least one non aqueous solvent, preferably selected from is benzyl alcohol, purified diethylene glycol monoethyl ether and/or NMP,
wherein the pH of the composition is comprised between about 6.5 and 8.5, when measured by adding 25% of water to an aliquot of said composition.

In a further most preferred embodiment the present invention refers to a veterinary or pharmaceutical composition comprising:
 (i) about 1-65% w/v of a pyrethroid, or a salt thereof, wherein the pyrethroid is preferably an isomeric mixture comprising a cis/trans ratio of about 40/60,
 (ii) a macrocyclic lactone, or a salt thereof, wherein the macrocyclic lactone is present in an amount of about 0.05-25% w/v of the total composition, and is preferably moxidectin
 (iii) at least one alkalizing agent, wherein the alkalizing agent is present in an amount of from 0.0001% to 1% w/v of the total composition
 (iv) at least one non aqueous solvent, preferably selected from is benzyl alcohol, purified diethylene glycol monoethyl ether and/or NMP,
wherein the pH of the composition is comprised between about 6.5 and 8.5, when measured by adding 25% of water to an aliquot of said composition.

In a further most preferred embodiment the present invention refers to a veterinary or pharmaceutical composition comprising:
 (i) about 50% w/v of permethrin or a salt thereof,
 (ii) about 2.5% w/v of moxidectin,
 (iii) about 0.0001 to 1% w/v of sodium hydroxide solution at 32 w % and/or about 0.5% w/v of sorbate potassium,
 (iv) benzyl alcohol,
wherein the pH of the composition is comprised between about 7.1 and 7.7, when measured by adding 25% of water to an aliquot of said composition.

Another object of the invention is a veterinary or pharmaceutical composition comprising:
 (i) about 1-65% w/v of a pyrethroid, or a salt thereof, preferably about 25-65% w/v of permethrin, or a salt thereof,
 (ii) a macrocyclic lactone, or a salt thereof,
 (iii) at least one alkalizing agent,
 (iv) at least one non aqueous solvent,
wherein the pH of the composition is comprised between about 6.5 and 8.5, when measured by adding 25% of water to an aliquot of said composition, for use in preventing and/or treating parasites infestations in a non-human mammal.

According to the present invention, non-human mammals refers to companion animals, or pets, or any domesticated animals, and includes, without any limitation, dogs, puppies, cats, kitten, rabbits, sheep, goats, pigs, cows, gerbils, horses, mice, ferrets, hamsters, horses, and the like. In a preferred embodiment, the non-human mammal is a pet, such as a canine, or such as a cat, more preferably is a dog. The dog can be a small size dog, a medium size dog or a large size dog.

"Preventing and/or treating" as used herein include the control, the reduction, the progression slowing, the eradication, the cure and/or avoid parasites infestations.

In a particular embodiment, the composition is administered, more precisely topically administered, which means line-on or spot-on, every month. It has as an efficacy of 1 month or more, up to 3 months, for example 6 weeks, 2 months, 10 weeks, or 3 months, preferably the composition is administered every 3 to 12 weeks, more preferably every 4 to 10 weeks, more preferably every 4 to 8 weeks, more preferably every 4 to 6 weeks, even more preferably once per month. "Efficacy" used herein refers to a therapeutically effective amount of the active substance to treat and/or prevent diseases. Examples of effective dosages (pipette volume), in dogs, are:

For 25 mg/mL of moxidectin and 500 mg/mL of permethrin, in a pipette (pipette volumes):
X-small dogs (equal of <4 kg): 0.4 mL,
Small dogs (>4-10 kg): 1 mL,
Medium dogs (>10-25 kg): 2.5 mL,
Large dogs (>25-40 kg): 4 mL,
X-Large dogs (>40-60 kg): 6 mL, For 20 mg/mL of moxidectin and 400 mg/mL of permethrin, in a pipette (pipette volumes):
X-Small dogs (equal of <4 kg): 0.5 mL,
Small dogs (>4-10 kg): 1.25 mL,
Medium dogs (>10-25 kg): 3.125 mL,
Large dogs (>25-40 kg): 5 mL,
X-Large dogs (>40-60 kg): 7.5 mL, In a preferred embodiment, the plasma concentration in the animal dosed at 2.5 mg/kg of moxidectin is above 0.025 ng/mL, for a period of at least 1 month, or of 1 month, or for a period of at least 6 weeks, or of 6 weeks, or for a period of at least 2 months, or of 2 months.

The composition according to the invention is in the form of a liquid solution, semi-liquid solution, suspension, paste, cream, foam, ointment, or gel. The composition is administered topically, by spot-on route, more especially line-on route. More especially, the composition is a ready-to-use spot-on composition.

"Administered" herein, and more precisely "line-on", means the composition is applied on the skin of the animal, from the base of the tail along the spine to the shoulder blades, or from the middle of the back along the spine to the shoulder blades, or less: the length of the "line-on" application can for example be 30 cm, or 20 cm, or 15 cm, or 10 cm, or 5 cm, the preferred length being 10 cm.

Composition is formulated as a unit dose adapted to the weight and/or size of the animal, and the entire dose is applied to the animal. Thanks to the line-on application method, the amount of diffused moxidectin through the animal skin and the amount of permethrin on the animal skin are known and controlled.

According to the present invention, parasites infestations are caused by mosquitoes, and/or fleas, and/or ticks, and/or nematodes, and/or lice, and/or flies, and/or sandflies, and/or mites, and/or blowfly, and/or mange, more especially by mosquitoes, and/or fleas, and/or ticks, and/or nematodes.

In an embodiment according to the present application, the ectoparasite is a tick, which is from the families Argasidae and/or Ixodidae. The genera are:
*Hyalomma* spp.: *marginatum, dromedarii, aegypticum*
*Otobius* spp.: *megnini*
*Ornithodoros* spp.: *moubata, porcinus*
*Amblyomma* spp.: *americanum,* cajenniense, *hebraeum, maculatum, variegatum*
*Dermacentor* spp.: *reticulatus, variabilis, venustus, pictus, andersoni*
*Haemaphysalis* spp.: *bispinosa, concinna, leachi, punctata*
*Rhipicephalus* spp.: *appendiculatus, bursa, capensis, evertsi, sanguineus, simus*
*Ixodes* spp.: *canisuga, hexagonus, ricinus, holocyclus, pacificus, persulcatus, rubicundus, scapularis, dammini, pilosus*
*Boophilus* spp.: *annulatus, mircoplus.*
More precisely, the dog ticks are: *Otobius, Ornithodoros, Amblyomma, Dermacentor, Haemaphysalis, Hyalomma, Ixodes, Rhipicephalus* and *Boophilus.* The cat ticks are: *Otobius, Ornithodoros, Amblyomma, Dermacentor, Haemaphysalis, Ixodes* and *Rhipicephalus.*

The preferred tick are *Dermacentor* spp., *Rhipicephalus* spp. or *Ixodes* spp.

In another embodiment of the invention, the ectoparasite is a flea. Cat and dog fleas are from the families Pulicidae and/or Ceratophyllidae:
*Ceratophyllus* spp.: *gallinae*
*Ctenocephalides* spp.: *canis, felis*
*Pulex* spp.: *irritans*
*Spilopsyllus* spp.: *cuniculli*
*Archaeopsylla* spp.: *erinacei*
*Echidnophaga* spp.: *gallinacea.*

The preferred flea is *Ctenocephalides* spp. (more especially *felis*).

In another embodiment of the invention, the ectoparasite is a louse. Cat lice are from the family Trichodectidae:
*Felicola* spp.: *subrostratus*

Dog lice are from the families Linognathidae and/or Trichodectidae:
*Linognathus* spp.: *setosus*
*Trichodectes* spp.: *canis*

In another embodiment of the invention, the ectoparasite is a mite. Cat mites are from the families Demodicidae, Psoroptidae, Sarcoptidae, Cheyletidae, Dermanyssidae and/or Trombiculidae:
*Demodex* spp.: *cati*
*Otodectes* spp.: *cynotis*
*Notoedres* spp.: *cati*
*Sarcoptes* spp.: *scabiei*
*Cheyletiella* spp.: *blakei, parasitovorax*
*Dermanyssus* spp.: *gallinae*
*Neotrombicula* spp.: *autumnalis*

The preferred mite is *Demodex* spp. or *Sarcoptes* spp.

Cat and dog mites are from the families Boopidae, Cheyletidae, Psoroptidae, Sarcoptidae, Demodicidae, Dermanyssidae and/or Trombiculidae:
*Cheyletiella* spp.: *yasguri*
*Otodectes* spp.: *cyanoti*
*Sarcoptes* spp.: *scabiei*
*Notoedres* spp.: *cati*
*Demodex* spp.: *canis*
*Dermanyssus* spp.: *gallinae*
*Neotrombicula* spp.: *autumnalis.*

The preferred mite is *Sarcoptes* spp. Or *Demodex* spp.

In another embodiment of the invention, the ectoparasite is a fly. Cat and dog flies are from the families Calliphoridae, Sarcophagidae, Psychodidae and/or Oestridae:
*Cordylobia* spp.: *anthropophaga*
*Cochliomyia* spp.: *hominivorax, macellaria*
*Chrysomya* spp.: *bezziana, megacephala*
*Wohlfahrtia* spp.: *magnifica, meigeni, vigil*
*Dermatobia* spp.: *hominis.*
*Phlebotomus* spp.: *papatasi, perniciosus*
*Lutzomyia* spp.: *longipalpis, verrucarum, adiketis*

The preferred fly is *phlebotomus* spp or *lutzomyia* spp.

In another embodiment of the invention, the ectoparasite is a mosquitoe. Cat and dog mosquitoes are from the familiy Culicidae:
*Aedes* spp.: *cinereus, esoensis rossicus, vexans, vittatus, aegypti, albopictus* . . . .
*Anopheles* spp.: *anopheles, cellia, kerteszia, lophodomyia, nyssorhynchus, stethomyia, baimaia*
*Culex* spp.: *pipiens, anips, apicalis, conservator, corniger, pilosus, reevesi, adami, rubinotus* . . . .

*Ochlerotatus* spp.: *acartomyia, culicelsa, gilesia, protoculex, empihals, pholeomyia, sallumia, buvirillia, caspius* . . . .

*Uranotaenia* spp.: *abdita, nigerrima, nigerrima, harrisoni, yunnanensis, pifanoi, leucoptera, gerdae, campestris, grasse, mayottensis, mashonaensis, madagascarensis* . . . .

The preferred mosquitoe are *Aedes aegypti*, *Aedes albopictus* and *Culex pipiens*.

The above list is not exhaustive and other ectoparasites are well known in the art to be harmful to animals and humans. These include for example migrating dipterous larvae.

The composition according to the invention can also be used to treat against endoparasites, more especially hookworms, flatworms, tapeworms, more especially gastro-intestinal nematodes, cardio-pulmonary nematodes and/or heartworms.

In one embodiment of the invention, the endoparasite is a nematode, cestode, trematode and/or acanthocephalans in small intestine. Cat worms are from the families Ascaridoidea, Ancylostomoidea, Rhabditoidea, Diphyllobotrhiidae, Dilepididae, Taeniidae, Diphyllobothriidae, Mesocestoididae, Diplistomatidae, Heterophydiae, Echinostomatidae, Pliganthorynchidae and/or Trichuroidea:

*Toxoscaris* spp.: *leonina*
*Toxocara* spp.: *mystax, malayensis*
*Ancylostoma* spp.: *braziliense, ceylanicum, tibaeforme*
*Uncinaria* spp.: *stenocephala*
*Strongyloides* spp.: *stercocoralis, planiceps, felis, tumefaciens*
*Diphyllobothrium* spp.: *latum, caninum*
*Echinococcus* spp.: *multilocularis, oligarthrus*
*Spirometra* spp.: *masoni, mansonoides, erinacei*
*Taenia* spp.: *taeniaeformis*
*Mesocestoides* spp.: *lineatus*
*Alaria* spp.: *alata, minessotae, marcianae*
*Heterophyes* spp.: *heterophyes, nocens*
*Metagonimus* spp.: *yokogawai*
*Apophallus* spp.: *donicum, mulhingi*
*Cryptocotyle* spp.: *lingua*
*Echinochasmus* spp.: *perfoliatus*
*Euparyphium* spp.: *melis*
*Nanophyetus* spp.: *salmincola*
*Macracanthorhynchus* spp.: *hirudinaceus, catalinum*
*Onicola* spp.: *campanulatus*
*Trichinella* spp.: *serrata, vulpis, campanula*.

Dog worms are from the families Ascaridoidea, Ancylostomoidea, Rhabditoidea, Diphyllobotrhiidae, Dilepididae, Taeniidae, Diphyllobothriidae, Mesocestoididae, Diplistomatidae, Heterophydiae, Echinostomatidae, Pliganthorynchidae and/or Trichuroidea:

*Toxocara* spp.: *canis*
*Toxoscaris* spp.: *leonina*
*Ancylostoma* spp.: *caninum, braziliense, ceylanicum*
*Uncinaria* spp.: *stenocephala*
*Strongyloides* spp.: *stercoralis*
*Diphyllobothrium* spp.: *latum, caninum*
*Echinococcus* spp.: *granulosus, quinus, orteleppi, multilocularis, vogeli*
*Spirometra* spp.: *masoni, mansonoides*
*Taenia* spp.: *hydatigena, multiceps, ovis, pisiformis, serialis, crassiceps*
*Mesocestoides* spp.: *lineatus*
*Alaria* spp.: *alata, americana, canis, michiganensis*
*Heterophyes* spp.: *heterophyes, nocens*
*Metagonimus* spp.: *yokogawai*
*Apophallus* spp.: *donicum, mulhingi*
*Cryptocotyle* spp.: *lingua*
*Echinochasmus* spp.: *perfoliatus, ilocanum*
*Nanophyetus* spp.: *salmincola*.

The preferred intestinal worms are *Toxocara* spp. (especially *canis*), *Toxoscaris* spp. (especially *leonina*), *Ancylostoma* spp. (especially *caninum*), *Trichuris* spp. (especially *vulpis*) and *Uncinaria* spp. (especially *stenocephala*).

In another embodiment of the invention, the endoparasite is a nematode and/or a trematode in circulatory system. Cat worms are from the families Schistosomatidae and/or Filarioidae:

*Schistosoma* spp.: *japonicum, rodhaini*
*Dirofilaria* spp.: *immitis*
*Brugia* spp.: *pahangi, malayi*

Dog worms are from the families Schistosomatidae, Metastrongylidea and/or Filarioidae:

*Angiostrongylus* spp.: *vasorum*
*Schistosoma* spp.: *japonicum, spindale, incognitum*,
*Heterobilharzia* spp.: *americana*
*Dirofilaria* spp.: *immitis*
*Brugia* spp.: *pahangi, malayi*.

The preferred circulatory system worm is *Dirofilaria* spp. (heartworm).

In another embodiment of the invention, the cat and dog endoparasite is a nematode in subcutaneous tissues: *Dirofilariae* spp.: *repens*.

Further with or without the addition of additional pesticidal agents the composition of the invention can also be used to treat and/or prevent other pests which include but are not limited to pests:

from the order Isopoda, for example Oniscusasellus, Armadillidiumvulgare and Porcellioscaber;
from the order Diplopoda, for example Blaniulusguttulatus;
from the order Chilopoda, for example Geophiluscarpophagus and *Scutigera* spp.;
from the order Symphyla, for example Scutigerellaimmaculata;
from the order Thysanura, for example Lepismasaccharina;
from the order Collembola, for example Onychiurusarmatus;
from the order Orthoptera, for example Achetadomesticus, *Gryllotalpa* spp., Locustamigratoriamigratorioides, *Melanoplus* spp. and Schistocercagregaria;
from the order Blattaria, for example Blattaorientalis, Periplanetaamericana, Leucophaeamaderae and Blattellagermanica;
from the order Dermaptera, for example Forficulaauricularia;
from the order Isoptera, for example *Reticulitermes* spp.;
from the order Phthiraptera, for example Pediculushumanuscorporis, *Haematopinus* spp., *Linognathus* spp., *Trichodectes* spp. and *Damalinia* spp.;
from the order Thysanoptera, for example Hercinothripsfemoralis, Thripstabaci, Thripspalmi and Frankliniellaaccidentalis;
from the order Heteroptera, for example *Eurygaster* spp., Dysdercusintermedius, Piesmaquadrata, Cimexlectularius, Rhodniusprolixus and *Triatoma* spp.;
from the order Homoptera, for example Aleurodesbrassicae, Bemisiatabaci, Trialeurodesvaporariorum, *Aphis gossypii*, Brevicorynebrassicae, Cryptomyzusribis, *Aphis fabae, Aphis pomi*, Eriosomalanigerum, Hyalopterusarundinis, Phylloxeravastatrix, Pemphigus spp., Macrosiphumavenae, *Myzus* spp., Phorodonhumuli, Rhopalosiphumpadi, *Empoasca* spp., Euscelisbilobatus, Nephotettixcincticeps, Lecaniumcorni, Saissetiaoleae, Laodelphaxstriatellus, Nilaparvatalugens, Aonidiellaaurantii, Aspidiotushederae, *Pseudococcus* spp. and *Psylla* spp.;

from the order Lepidoptera, for example Pectinophoragossypiella, Bupaluspiniarius, Cheimatobiabrumata, Lithocolletisblancardella, Hyponomeutapadella, Plutellaxylostella, Malacosomaneustria, Euproctischysorrhoea, *Lymantria* spp., Bucculatrixthurberiella, Phyllocnistiscitrella, *Agrotis* spp., *Euxoa* spp., *Feltia* spp., Eariasinsulana, *Heliothis* spp., *Helicoverpa* spp., Mamestrabrassicae, Panolisflammea, *Spodoptera* spp., Trichoplusiani, Carpocapsapomonella, *Pieris* spp., *Chilo* spp., Pyraustanubilalis, Ephestiakuehniella, *Galleria mellonella*, Tineolabisselliella, Tineapellionella, Hofmannophilapseudospretella, Cacoeciapodana, *Capua reticulana*, Choristoneurafumiferana, Clysiaambiguella, Homonamagnanima, Tortrixviridana and Cnaphalocerus spp.;

from the order Coleoptera, for example Anobiurpunctatum, Rhizoperthadominica, Bruchidiusobtectus, Acanthoscelidesobtectus, Hylotrupesbajulus, Agelasticaalni, Leptinotarsadecerlineata, Phaedoncochleariae, *Diabrotica* spp., Psylliodeschrysocephala, Epilachnavarivestis, *Atomaria* spp., Oryzaephilussurinamensis, *Anthonomus* spp., *Sitophilus* spp., Otiorrhynchussulcatus, *Cosmopolites sordidus*, Ceuthorrhynchusassimilis, Hyperapostica, Dermestes spp., *Trogoderma* spp., *Anthrenus* spp., *Attagenus* spp., *Lyctus* spp., Meligethesaeneus, Ptinus spp., Niptushololeucus, Gibbiurpsylloides, *Tribolium* spp., Tenebriomolitor, *Agriotes* spp., Conoderus spp., Melolonthamelolontha, Amphimallonsolstitialis and Costelytrazealandica;

from the order Hymenoptera, for example *Diprion* spp., *Hoplocampa* spp., *Lasius* spp., Monomoriumpharaonis and *Vespa* spp.;

from the order Diptera, for example *Aedes* spp., *Anopheles* spp., *Culex* spp., *Drosophila melanogaster, Musca* spp., *Fannia* spp., Calliphoraerythrocephala, *Lucilia* spp., *Chrysomyia* spp., *Cuterebra* spp., *Gastrophilus* spp., *Hyppobosca* spp., *Stomoxys* spp. (*calcitrans* . . . ), *Oestrus* spp., *Hypoderma* spp., *Tabanus* spp., *Tannia* spp., Bibiohortulanus, *Oscinella frit, Phorbia* spp., Pegomyiahyoscyami, Ceratitiscapitata, Dacusoleae, Tipulapaludosa, *Hylemyia* spp. and *Liriomyza* spp.;

from the order Siphonaptera, for example XenopsyllacheopisandCeratophyllus spp.;

from the class of arachnids, for example Scorpio maurus, Latrodectusmactans, Acarussiro, *Argas* spp., *Ornithodoros* spp., Dermanyssusgallinae, Eriophyesribis, Phyllocoptrutaoleivora, *Boophilus* spp., *Rhipicephalus* spp., *Amblyomma* spp., *Hyalomma* spp., *Ixodes* spp., *Psoroptes* spp., Chorioptes spp., *Sarcoptes* spp., *Tarsonemus* spp., Bryobiapraetiosa, *Panonychus* spp., *Tetranychus* spp., *Hemitarsonemus* spp. and *Brevipalpus* spp.

In this application, each genera include all the associated species.

Another object of the present invention is a method of treatment and/or prevention of parasites infestations in a non-human mammal, comprising administering, more especially topically administering, to said non-human mammal a veterinary or pharmaceutical composition comprising:
(i) about 1-65% w/v of a pyrethroid, or a salt thereof, and
(ii) a macrocyclic lactone, or a salt thereof,
(iii) at least one alkalizing agent,
(iv) at least one non aqueous solvent,
wherein the pH of the composition is comprised between about 6.5 and 8.5, when measured by adding 25% of water to an aliquot of said composition.

Another object of the present invention is a use of a composition comprising:
(i) about 1-65% w/v of a pyrethroid, or a salt thereof, and
(ii) a macrocyclic lactone, or a salt thereof,
(iii) at least one alkalizing agent,
(iv) at least one non aqueous solvent,
having a pH comprised between about 6.5 and 8.5, when measured by adding 25% of water to an aliquot of said composition;
for making a drug for treating and/or preventing parasites infestations in a non-human mammal.

Another object of the present invention is a kit useful in preventing and/or treating parasites in a non-human mammal comprising a composition as described above, within a unique chamber pipette equipped with an applicator tip. The unique chamber pipette can have five dosages: 0.4 mL, 1 mL, 2.5 mL, 4 mL and 6 mL.

All embodiments described above for the composition also apply to the use of said composition, to the method of treatment, and to kit comprising said composition, as described below.

Described herein below are examples: preparation of compositions according to the present invention and efficiency tests. These examples are illustrative and in no way limiting.

EXAMPLES

Example 1: Comparative Example

TABLE 1 comparative example

| Ingredients (mg/ml) | A14 | A16 | B38 | A55 | A133 | A62 | A79 | C30 | Z32 |
|---|---|---|---|---|---|---|---|---|---|
| moxidectin | 25 | 25 | 25 | 25 | 25 | | | 25 | 25 |
| eprinomectin | | | | | | 3 | | | |
| ivermectin | | | | | | | 3 | | |
| permethrin | 500 | 500 | 500 | 500 | 500 | 525 | 525 | | |
| flumethrin | | | | | | | | 25 | |
| cyphenothrin | | | | | | | | | 200 |
| methoprene | | | | | | | | | 92.1 |
| BHT | | 0.5 | | 1 | 0.5 | | | | |
| vitamin E | | | | | | | | | 53 |
| potassium sorbate | | | | 0.04 | 0.1 | | | | |

TABLE 1-continued comparative example

| | Ingredients (mg/ml) | A14 | A16 | B38 | A55 | A133 | A62 | A79 | C30 | Z32 |
|---|---|---|---|---|---|---|---|---|---|---|
| | propylene carbonate | | | 83 | | | | | 83 | |
| | benzyl alcohol | | | QS 1 mL | | | | | QS 1 mL | |
| | DMSO | 30 | 30 | | 150 | | QS 1 mL | QS 1 mL | | |
| | diethylene glycol monoethyl ether | QS 1 mL | QS 1 mL | | QS 1 mL | | | | | QS 1 mL |
| | NOP | | | | | 66 | | | | |
| | NMP | | | | | QS 1 mL | | | | |
| | pH (according to drug composition method) | 4.5 | 4.5 | 2.9 | 5.1 | 5.5 | 4.5 | 4.5 | 4.3 | 4.9 |
| T = 0 | moxidectin assay (mg/mL) | 24.6 | 24.7 | 19.9 | 24.8 | 24.8 | | | 24.9 | 25 |
| | moxidectin degradation product (%) | 3.1 | 3.1 | 19.1 | 2.3 | 2.3 | | | 2.3 | 2.2 |
| | eprinomectin assay (mg/mL) | | | | | | 3 | | | |
| | eprinomectin degradation product (%) | | | | | | 3.6 | | | |
| | ivermectin assay (mg/mL) | | | | | | | 2.9 | | |
| | ivermectin degradation product (%) | | | | | | | 4.8 | | |
| after storage at 40° C./75% relative humidity (RH) | lactone macrocydic assay (mg/mL) | 22.4 | 22.4 | — | 23.8 | 22.1 | 2.78 | 2.1 | 22.5 | 22.8 |
| | lactone macrocydic degradation product (%) | 13.4 | 14.3 | — | 6.2 | 12.5 | 8.9 | 28.4 | 10.8 | 6.7 |

This example shows that the tested comparative compositions lead to low pH values and thus to poor stability results, and a fast increase of lactone macrocyclic degradation products is observed: more than 3.5% after two to six weeks at 40° C./75% RH.

Example 2: Stable Compositions Using Alkalizing Agent

In a manufacturing vessel, a portion of liquid vehicle(s), pyrethroid material, alkalizing agent(s) are added under stirring. Then antioxidant(s) if any, and macrocyclic lactone are added. Finally the final targeted volume is completed with liquid vehicle(s).

The following method is used to measure the composition pH: in a centrifuge tube, 75 v % (% volume) of drug composition and 25 v % of purified water are added. The blend is homogenized using a vortex equipment, then centrifuged and the pH of the upper phase (which means the water based phase) is determined.

TABLE 2 examples according to the present invention

| Ingredients (mg/mL) | B176 | B177 | B178 | B117 | Z32 | B179 | B118 | B180 | A99 | B119 | B132 | B106 | B120 | B41 | Z30 |
|---|---|---|---|---|---|---|---|---|---|---|---|---|---|---|---|
| Permethrin batch # | EA9 | EA9 | AJ2 | FD7 | FD7 | FD7 | 83 | 113 | 113 | EA7 | FD7 | 113 | 44 | | |
| Flumethrin batch # | | | | | | | | | | | | | | | 003/17 |
| Moxidectin | 25 | 25 | 25 | 25 | 25 | 25 | 25 | 25 | 25 | 25 | 25 | 25 | 25 | | 25 |
| Eprinomectin | | | | | | | | | | | | | | 1.5 | |
| Permethrin | 500 | 500 | 500 | 500 | 500 | 500 | 500 | 500 | 500 | 500 | 500 | 500 | 500 | 525 | |
| Flumethrin | | | | | | | | | | | | | | | 25 |
| Carbonate Propylene | 83 | 83 | 83 | 83 | 83 | 83 | 83 | 83 | 83 | 83 | 83 | 83 | 83 | | 83 |
| Sorbate potassium | | | | | | 0.3 | | | 0.5 | | | 0.3 | | 1 | |
| Butyl Hydroxy Toluene | | | | | | | | | 0.5 | | | | | | 0.5 |
| Sodium hydroxide solution at 32 w % | 1.2 | 1.7 | 1.3 | 1.2 | 1.2 | 1.2 | 1.6 | 0.75 | | 0.25 | 0.11 | 0.7 | 0.25 | | 0.01 |
| Vitamin E | | | | | | | | | | | 10 | | 10 | | |
| Polyvinyl pyrrolidone K30 | | | | 10 | | | | | | | | | | | |
| Benzyl alcohol | QS | QS | QS | QS | QS | QS | QS | QS | QS | QS | QS | | | | QS |
| Dimethyl sulfoxide | | | | | | | | | | | | 30 | 30 | | |
| Diethylene glycol monoethyl ether | | | | | | | | | | | | QS | QS | QS | |
| pH (according to drug composition method) | 7.3 | 7.6 | 7.6 | 7.4 | 7.4 | 7.7 | 7.7 | 7.7 | 7.1 | 7.5 | 7.1 | 6.5 | 8.5 | 8.2 | 7.7 |

TABLE 2bis

Stability of the compositions of the invention

| Formula batch # | 40° C./75% RH | | | | 30° C./65% RH | | | | 25° C./60% RH | | | | | |
|---|---|---|---|---|---|---|---|---|---|---|---|---|---|---|
| | T0 | T1.5M | T3M | T6M | T6M | T9M | T12M | T18M | T3M | T6M | T9M | T12M | T18M | T24M |
| | | | | | Moxidectin assay (mg/mL) | | | | | | | | | |
| A99 | 24.7 | 24.9 | 24.7 | 24.5 | 24.6 | — | 24.7 | 25.3 | 24.8 | 24.7 | — | 24.8 | 25.1 | 24.0 |
| B118 | 25.2 | 24.8 | 24.6 | 24.5 | 25.1 | 25.0 | 24.6 | — | 25.1 | 25.2 | 25.3 | 25.3 | — | — |
| B119 | 24.6 | 24.3 | 24.7 | 24.5 | 24.7 | 24.7 | 23.8 | — | 24.7 | 24.7 | 24.8 | 23.8 | — | — |
| | | | | | Total moxidectin degradation products (%) | | | | | | | | | |
| A99 | <0.2 | 0.6 | 0.9 | 2.0 | 0.7 | — | 1.2 | 1.6 | 0.2 | 0.4 | — | 0.9 | 1.2 | 1.8 |
| B118 | <0.2 | 0.4 | 1.3 | 1.7 | 0.4 | 1.1 | 1.4 | — | 0.4 | 0.2 | 0.5 | 0.6 | — | — |
| B119 | <0.2 | 0.3 | 0.4 | 0.4 | 0.2 | 20.4 | 0.5 | — | 0.3 | 0.2 | 0.2 | 0.2 | — | — |
| | | | | | Permethrin assay (mg/mL) | | | | | | | | | |
| A99 | 491 | 493 | 494 | 497 | 490 | — | 508 | 507 | 494 | 495 | — | 507 | 510 | 500 |
| B118 | 512 | 514 | 515 | 503 | 507 | 512 | 512 | — | 516 | 507 | 514 | 511 | — | — |
| B119 | 508 | 508 | 511 | 507 | 502 | 507 | 505 | — | 512 | 501 | 508 | 503 | — | — |
| | | | | | Total permethrin degradation products (%) | | | | | | | | | |
| A99 | ND | ND | ND | ND | ND | — | ND | ND | ND | ND | — | ND | ND | ND |
| B118 | ND | ND | ND | ND | ND | ND | ND | — | ND | ND | ND | ND | — | — |
| B119 | ND | ND | ND | ND | ND | ND | ND | — | ND | ND | ND | ND | — | — |

ND—Not detected

All these formulae are chemically stable for each tested condition (less than 3.5% moxidectin degradation is observed and no permethrin degradation product detected).

All these formulae are physically stable from −20° C. to 40° C. during at least 1 week.

Example 3: Tests on Mosquitoes

The repellency, knock-down and killing efficiency of the composition according to the present invention) has been measured. The study protocol comprises the two following groups of eight dogs:
  group 1: untreated dogs (control),
  group 2: dogs treated with a composition according to the invention.

Dogs have been infested with mosquitoes (*Aedes aegypti*) at day −7. At day 0, group 2 has been treated with the with a composition according to the present invention. At days 1, 7, 14, 21, 28, 35 and 42 (and days 49 and 56 for tests in tables 6 and 8), dogs of the two groups have been infested with mosquitoes again. And, at these particular days, at 1 h and 24 hours after mosquitoes release, the fed (alive, moribund and dead, table 3), alive (tables 4 and 5) and alive and moribund (tables 6 and 7) mosquitoes has been counted. Two means have been calculated: geometric mean (GM) and arithmetic mean (AM).

Table 3: Repellency Efficiency (Alive, Moribund and Dead Mosquitoes)

The efficiency (%) is equal to 100×(Fc−Ft)/Fc, where:
  Fc is the mean number of fed mosquitoes in group 1,
  Ft is the mean number of fed mosquitoes in group 2.

Table 3 shows the repellency efficiency of the composition according to the invention.

TABLE 3

| | D1 | D7 | D14 | D21 | D28 | D35 | D42 |
|---|---|---|---|---|---|---|---|
| Group 2 (AM) | 87.1 | 95.7 | 93.5 | 90.6 | 91.6 | 80.0 | 56.5 |
| Group 2 (GM) | 88.0 | 96.9 | 93.5 | 93.4 | 92.7 | 88.3 | 62.2 |

TABLE 3-continued

| | D1 | D7 | D14 | D21 | D28 | D35 | D42 |
|---|---|---|---|---|---|---|---|
| Group 1 (AM) | 0 | 0 | 0 | 0 | 0 | 0 | 0 |
| Group 1 (GM) | 0 | 0 | 0 | 0 | 0 | 0 | 0 |

It can be concluded that the composition according to the present invention is efficient enough to repel mosquitoes during more than one month: higher than or equal to 90% (GM) and higher than or equal to 80% (AM).

Table 4: Immediate Knock-Down Efficiency (Alive Mosquitoes) at 60±5 Minutes after Release Table 4 shows the immediate knock-down efficiency (%) of the composition against mosquitoes at 60±5 minutes after release equal to 100×(Mkc−Mkt)/Mkc, where:
  Mkc is the mean number of alive mosquitoes in group 1,
  Mkt is the mean number of alive mosquitoes in group 2.

TABLE 4

| | D1 | D7 | D14 | D21 | D28 | D35 | D42 |
|---|---|---|---|---|---|---|---|
| Group 2 (AM) | 95.4 | 91.5 | 63.0 | 90.8 | 82.5 | 74.4 | 69.9 |
| Group 2 (GM) | 96.9 | 95.0 | 63.8 | 94.1 | 85.0 | 75.2 | 80.6 |
| Group 1 (AM) | 0 | 0 | 0 | 0 | 0 | 0 | 0 |
| Group 1 (GM) | 0 | 0 | 0 | 0 | 0 | 0 | 0 |

It can be concluded that the composition according to the present invention is efficient enough to knock-down more than 95% of mosquitoes 1 hour after infestation at day 1, and still more than 80% of mosquitoes at day 28.

Table 5: Knock-Down Efficiency (Alive Mosquitoes) at the End of Incubation

Table 5 shows the knock-down efficiency (%) of the composition against mosquitoes at the end of incubation (24 hours) equal to 100×(MLc−MLt)/MLc, where:
  MLc is the mean number of alive mosquitoes in group 1 at the end of incubation,
  MLt is the mean number of alive mosquitoes in group 2 at the end of incubation.

TABLE 5

|  | D1 | D7 | D14 | D21 | D28 | D35 | D42 | D49 | D56 |
|---|---|---|---|---|---|---|---|---|---|
| Group 2 (AM) | 99.3 | 97.7 | 97.0 | 100.0 | 99.7 | 99.4 | 95.5 | 97.2 | 90.4 |
| Group 2 (GM) | 99.5 | 99.1 | 98.5 | 100.0 | 99.8 | 99.6 | 98.9 | 98.8 | 95.3 |
| Group 1 (AM) | 0 | 0 | 0 | 0 | 0 | 0 | 0 | 0 | 0 |
| Group 1 (GM) | 0 | 0 | 0 | 0 | 0 | 0 | 0 | 0 | 0 |

It can be concluded that the composition according to the present invention is efficient enough to knock-down more than 99% of mosquitoes 24 hours after infestation at day 1, and still more than 98% of mosquitoes at day 42, and still more than 90% at day 56.

Table 6: Immediate Insecticidal Efficiency (Alive and Moribund Mosquitoes) at 60±5 Minutes after Release Table 6 shows the immediate insecticidal efficiency (%) against mosquitoes at 60±5 minutes after release equal to 100×(Mc−Mt)/Mc, where:

Mc is the mean number of alive and moribund mosquitoes in group 1,

Mt is the mean number of alive and moribund mosquitoes in group 2.

TABLE 6

|  | D1 | D7 | D14 | D21 | D28 | D35 | D42 |
|---|---|---|---|---|---|---|---|
| Group 2 (AM) | 50.4 | 88.3 | 54.8 | 38.3 | 23.1 | 35.8 | 8.5 |
| Group 2 (GM) | 74.3 | 92.2 | 55.4 | 41.9 | 26.7 | 38.6 | 29.9 |
| Group 1 (AM) | 0 | 0 | 0 | 0 | 0 | 0 | 0 |
| Group 1 (GM) | 0 | 0 | 0 | 0 | 0 | 0 | 0 |

It can be concluded that the composition according to the present invention is efficient enough to kill more than 74% of mosquitoes 1 hour after infestation at day 1, and still more than 40% of mosquitoes at day 21.

Table 7: Insecticidal Efficiency (Alive and Moribund Mosquitoes) at the End of Incubation Table 7 shows the insecticidal efficiency (%) at the end of incubation (24 h) against mosquitoes is equal to 100×(Mc−Mt)/Mc, where:

MLc is the mean number of alive or moribund mosquitoes in the negative control group (group 1)

MLt is the mean number of alive or moribund mosquitoes in group 2.

TABLE 7

|  | D1 | D7 | D14 | D21 | D28 | D35 | D42 | D49 | D56 |
|---|---|---|---|---|---|---|---|---|---|
| Group 2 (AM) | 99.0 | 98.5 | 95.5 | 99.2 | 98.9 | 89.7 | 95.1 | 96.7 | 82 |
| Group 2 (GM) | 99.3 | 99.4 | 97.4 | 99.4 | 99.0 | 92.6 | 98.6 | 98.3 | 88.9 |
| Group 1 (AM) | 0 | 0 | 0 | 0 | 0 | 0 | 0 | 0 | 0 |
| Group 1 (GM) | 0 | 0 | 0 | 0 | 0 | 0 | 0 | 0 | 0 |

It can be concluded that the composition according to the present invention is efficient enough to kill more than 99% of mosquitoes 24 hours after infestation at day 1, and still more than 95% of mosquitoes at day 42.

Example 4: Tests on Fleas

At day 29, group 2 treated with a composition according to the present invention has further been infested with fleas (*Ctenophalides felis*). The dead fleas have been counted at day 29+24 hours after infestation.

TABLE 8

|  | D30 |
|---|---|
| Group 2 (AM) | 87.7 |
| Group 2 (GM) | 94.1 |
| Group 1 (AM) | 0 |
| Group 1 (GM) | 0 |

It can be concluded that the composition according to the present invention is efficient enough to kill more than 87% of fleas at day 30.

Example 5: Tests on Ticks

At day 28, group 2 treated with a composition according to the present invention has further been infested with ticks (*Rhipicephalus sanguineus*). The dead ticks have been counted at day 28+24 hours after infestation and 48 hours after infestation.

TABLE 9

|  | D29 | D30 |
|---|---|---|
| Group 2 (AM) | 90.4 | 89.1 |
| Group 2 (GM) | 96.1 | 95.9 |
| Group 1 (AM) | 0 | 0 |
| Group 1 (GM) | 0 | 0 |

It can be concluded that the composition according to the present invention is efficient enough to kill more than 90% of ticks at day 29, and still more than 89% of ticks at day 30.

All these results indicate the composition according to the present invention is efficient enough to repel, knock-down and kill mosquitoes, ticks and fleas during more than one month.

The invention claimed is:

1. A veterinary or pharmaceutical composition comprising:
   (i) 45-55% w/v of a pyrethroid, or a salt thereof,
   (ii) 2-5% w/v of a macrocyclic lactone, or a salt thereof,
   (iii) at least one alkalizing agent in an amount ranging from 0.001% w/v to 0.3% w/v,
   (iv) at least one non-aqueous solvent,
   wherein the pH of the composition is between 7.2 and 8.5, when measured by adding 25% of water to an aliquot of said composition, and
   wherein the pyrethroid is permethrin, the macrocyclic lactone is moxidectin, the at least one alkalizing agent comprises sodium hydroxide, and the at least one non-aqueous solvent comprises benzyl alcohol, diethylene glycol monoethyl ether and/or N-methyl-2-pyrrolidone.

2. The veterinary or pharmaceutical composition according to claim 1, wherein permethrin is an isomeric mixture comprising a cis/trans ratio of 40/60.

3. The veterinary or pharmaceutical composition according to claim 1, wherein the macrocyclic lactone is present in an amount of 2.5% w/v of the total composition.

4. The veterinary or pharmaceutical composition according to claim 1, wherein the at least one non aqueous solvent is benzyl alcohol, purified diethylene glycol monoethyl ether and/or N-methyl-2-pyrrolidone.

5. The veterinary or pharmaceutical composition according to claim 1, wherein the composition is a ready-to-use, spot-on composition.

6. The veterinary or pharmaceutical composition according to claim 1, wherein the pyrethroid is present in an amount of 50% w/v of the total composition.

7. A kit useful in preventing and/or treating parasites in a non-human mammal comprising a composition as defined in claim 1, within a chamber pipette equipped with an applicator tip.

8. A method for preventing and/or treating a parasite infestation in a non-human mammal comprising topically administering in said non-human mammal the veterinary or pharmaceutical composition of claim 1.

9. The method according to claim 8, wherein the non-human mammal is a pet.

10. The method according to claim 9, wherein the pet is a canine.

11. The method according to claim 8, wherein the parasites infestations are caused by mosquitoes, fleas, ticks, and/or nematodes.

12. The method according to claim 8, wherein the composition is topically administered once per month.

13. A method of manufacturing a composition as defined in claim 1, comprising the steps of:
  (i) determining acid value (IA) of the pyrethroid,
  (ii) mixing all the components,
  (ii) adding in the composition about $0.0001 \times IA$ to $0.01 \times IA$ mg/mL of at least one alkalizing agent for each mg/mL of pyrethroid.

* * * * *